(12) United States Patent
Rachman et al.

(10) Patent No.: US 10,190,980 B2
(45) Date of Patent: Jan. 29, 2019

(54) SYSTEM AND METHOD FOR SIMULTANEOUS MEASUREMENT OF TURBIDITY, COLOR AND CHLORINE CONTENT OF A SAMPLE OF A LIQUID

(71) Applicant: BLUE-I WATER TECHNOLOGIES LTD., Rosh Haayin (IL)

(72) Inventors: Alex Rachman, Holon (IL); Mikhail Lifshits, Holon (IL); Stela Diamant Lazarovich, Herzilia Pituach (IL)

(73) Assignee: BLUE-I WATER TECHNOLOGIES LTD., Rosh Haayin (IL)

( * ) Notice: Subject to any disclaimer, the term of this patent is extended or adjusted under 35 U.S.C. 154(b) by 96 days.

(21) Appl. No.: 14/895,610

(22) PCT Filed: Jun. 2, 2014

(86) PCT No.: PCT/IL2014/050500
§ 371 (c)(1),
(2) Date: Dec. 3, 2015

(87) PCT Pub. No.: WO2014/195946
PCT Pub. Date: Dec. 11, 2014

(65) Prior Publication Data
US 2016/0131578 A1    May 12, 2016

Related U.S. Application Data

(60) Provisional application No. 61/830,271, filed on Jun. 3, 2013.

(51) Int. Cl.
| | |
|---|---|
| *G01N 21/00* | (2006.01) |
| *G01N 21/53* | (2006.01) |
| *G01N 21/25* | (2006.01) |
| *G01N 33/18* | (2006.01) |
| *G01N 21/51* | (2006.01) |
| *G01N 21/78* | (2006.01) |

(Continued)

(52) U.S. Cl.
CPC ........... *G01N 21/532* (2013.01); *G01J 3/46* (2013.01); *G01N 21/251* (2013.01);
(Continued)

(58) Field of Classification Search
CPC ........ G01N 21/53; G01N 21/25; G01N 33/18; G01N 21/50; G01N 21/78; G01J 3/46
See application file for complete search history.

(56) References Cited

U.S. PATENT DOCUMENTS

| | | |
|---|---|---|
| 5,107,133 A | 4/1992 | Klainer |
| 5,506,279 A | 4/1996 | Cooper et al. |

(Continued)

FOREIGN PATENT DOCUMENTS

| | | |
|---|---|---|
| CN | 1934743 B | 3/2007 |
| CN | 101281187 A | 10/2008 |

(Continued)

OTHER PUBLICATIONS

International Search Report dated Sep. 10, 2014.
(Continued)

*Primary Examiner* — Abdullahi Nur
(74) *Attorney, Agent, or Firm* — Symbus Law Group, LLC; Clifford D. Hyra

(57) ABSTRACT

A method for measuring turbidity, chlorine content and color of a liquid, the method including retaining, from a continuous flow of the liquid, a sample volume of the liquid, and at least nearly simultaneously executing at least two of detecting illumination from the sample volume of liquid by at least a first detector operable for detecting illumination from the sample volume of liquid at a 90-degree angle with respect to an illumination beam generated by an illuminator and impinging on the sample volume of liquid, thereby measuring a turbidity of the sample volume of liquid.

15 Claims, 15 Drawing Sheets

(51) Int. Cl.
  *G01J 3/46* (2006.01)
  *G01N 21/47* (2006.01)
  *G01N 21/05* (2006.01)
  *G01N 15/00* (2006.01)
  *G01J 3/50* (2006.01)
  *G01N 15/06* (2006.01)

(52) U.S. Cl.
  CPC ........... *G01N 21/255* (2013.01); *G01N 21/51* (2013.01); *G01N 21/78* (2013.01); *G01N 33/18* (2013.01); *G01J 3/50* (2013.01); *G01N 33/182* (2013.01); *G01N 2015/0053* (2013.01); *G01N 2015/0693* (2013.01); *G01N 2021/054* (2013.01); *G01N 2021/4711* (2013.01); *G01N 2021/4726* (2013.01)

(56) References Cited

U.S. PATENT DOCUMENTS

| | | | |
|---|---|---|---|
| 7,491,366 B2 * | 2/2009 | Tokhtuev | G01N 21/251 422/82.05 |
| 2003/0184754 A1 | 10/2003 | Bernhardsson | |
| 2003/0233723 A1 | 12/2003 | Lizotte et al. | |
| 2006/0198761 A1 | 9/2006 | Tokhtuev et al. | |
| 2007/0092406 A1 | 4/2007 | David | |
| 2010/0081552 A1 | 4/2010 | Chan | |

FOREIGN PATENT DOCUMENTS

| | | |
|---|---|---|
| CN | 101814228 A | 8/2010 |
| CN | 104592293 A | 2/2014 |
| CN | 104181280 A | 5/2016 |
| EP | 1252857 A2 | 10/2002 |
| WO | WO2998/057034 A1 | 5/2009 |

OTHER PUBLICATIONS

UK Office Action dated Jan. 30, 2018.
Chinese Office Action dated Jan. 17, 2018.
Australian Office Action dated Sep. 11, 2017.
Israel Office Action dated Apr. 7, 2018.
'TC-3000 Tri-Meters', 2005, [retrieved from Internet on Sep. 8, 2017], http://www.globalw.com/downloads/WQ/TC3000.pdf.

* cited by examiner

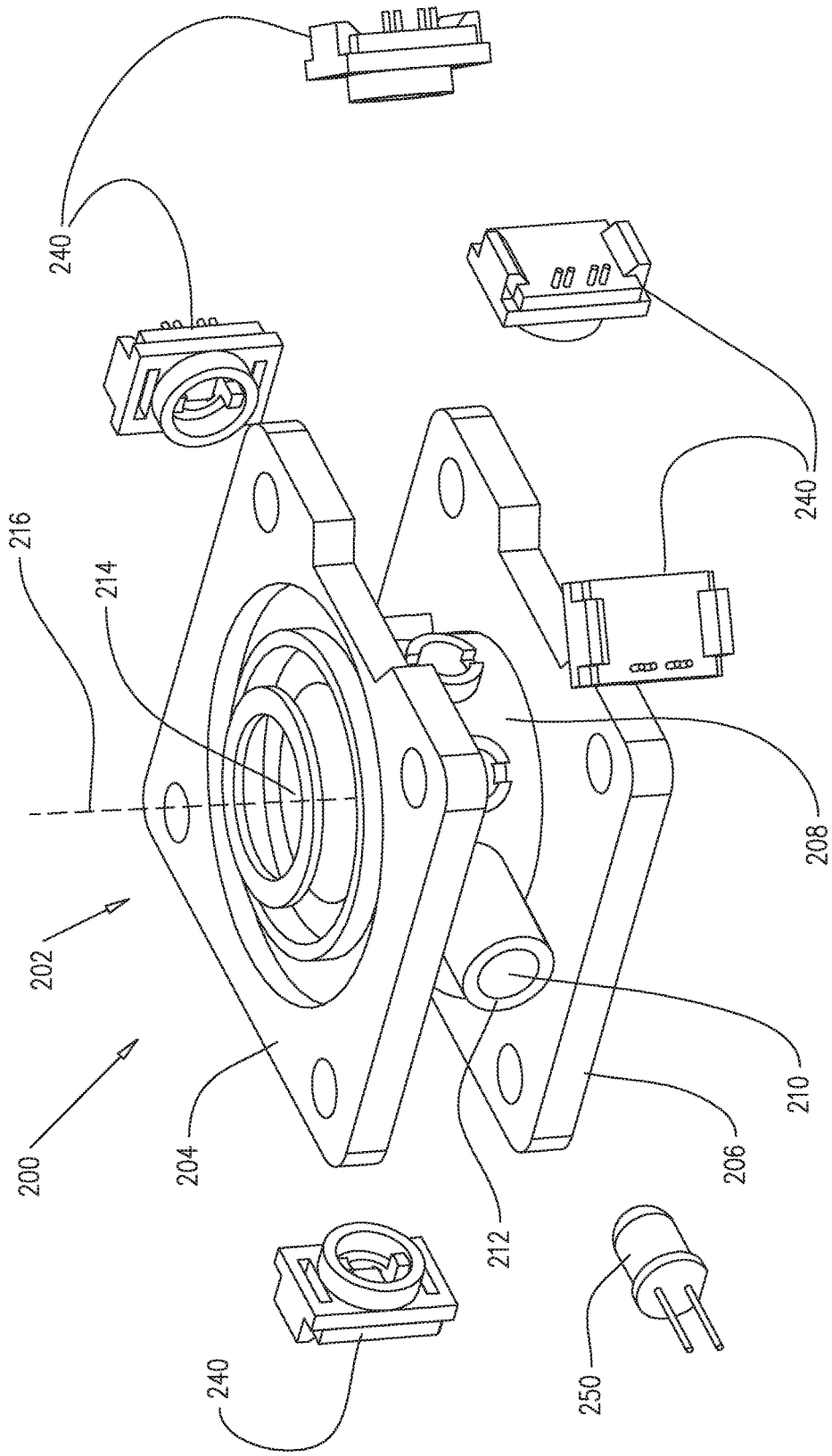

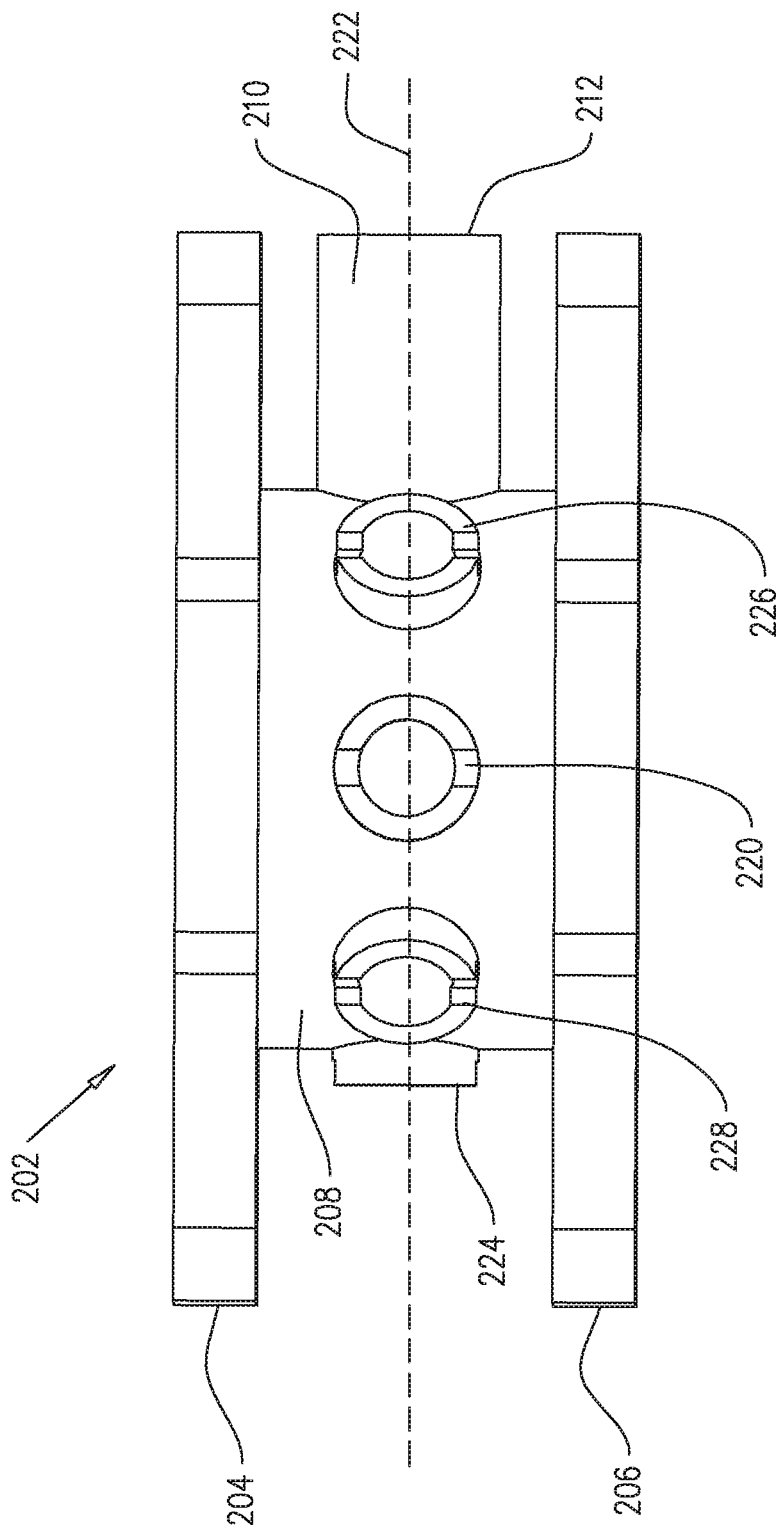

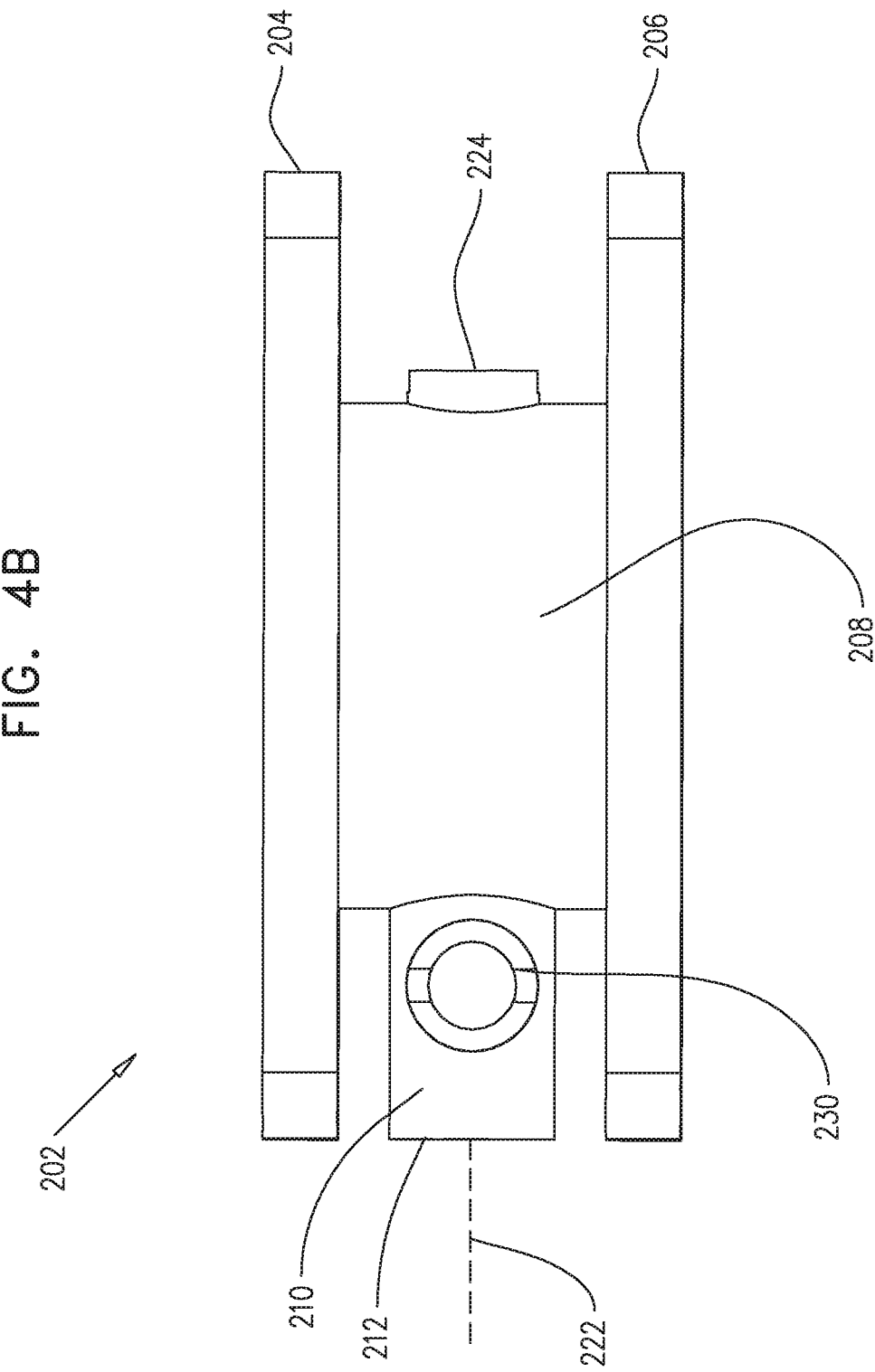

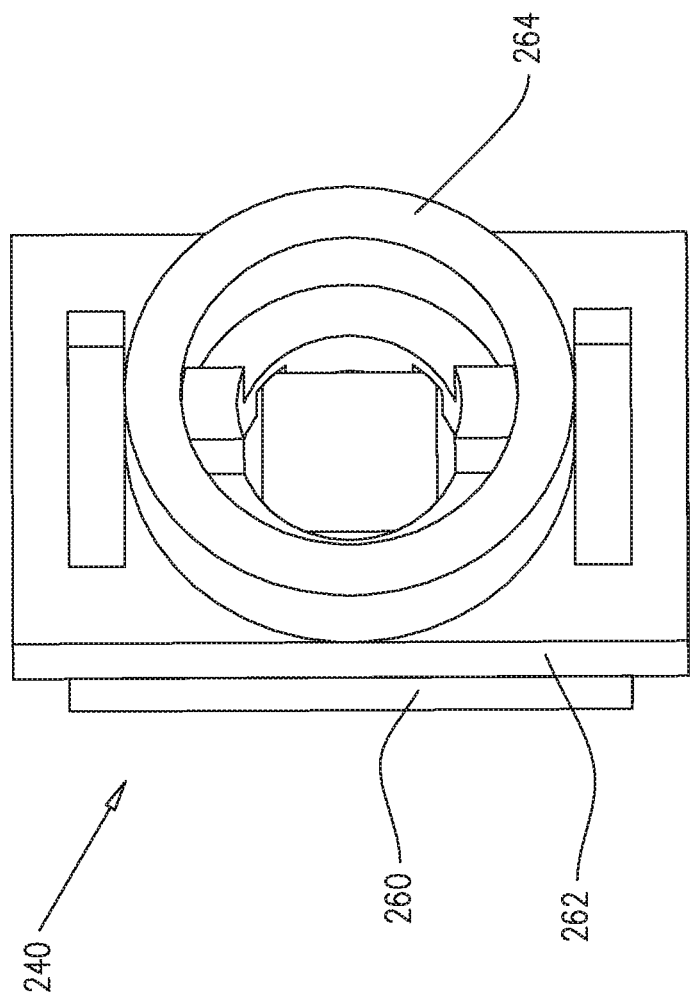

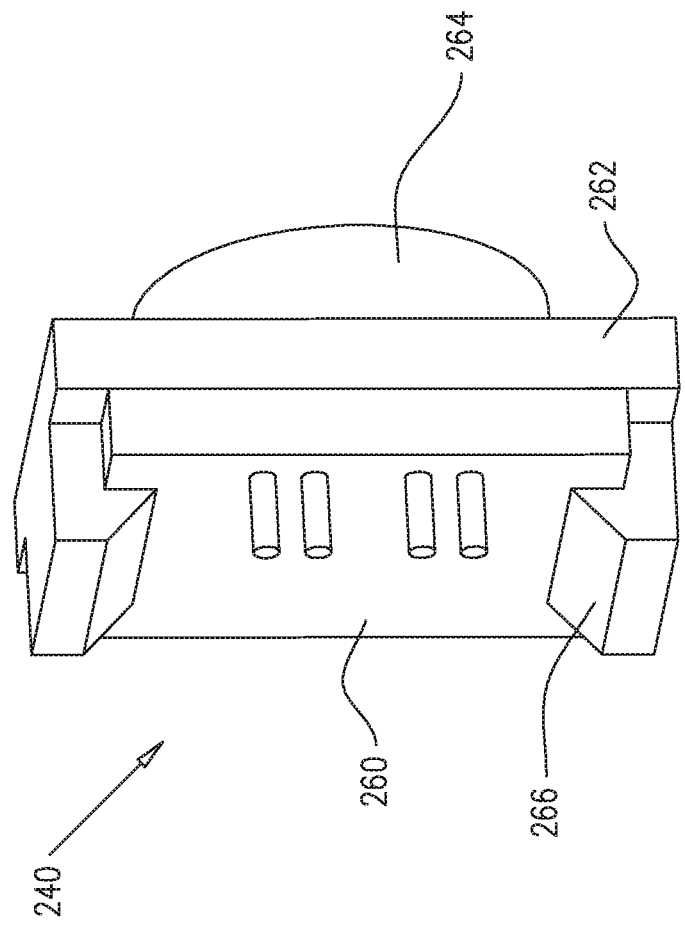

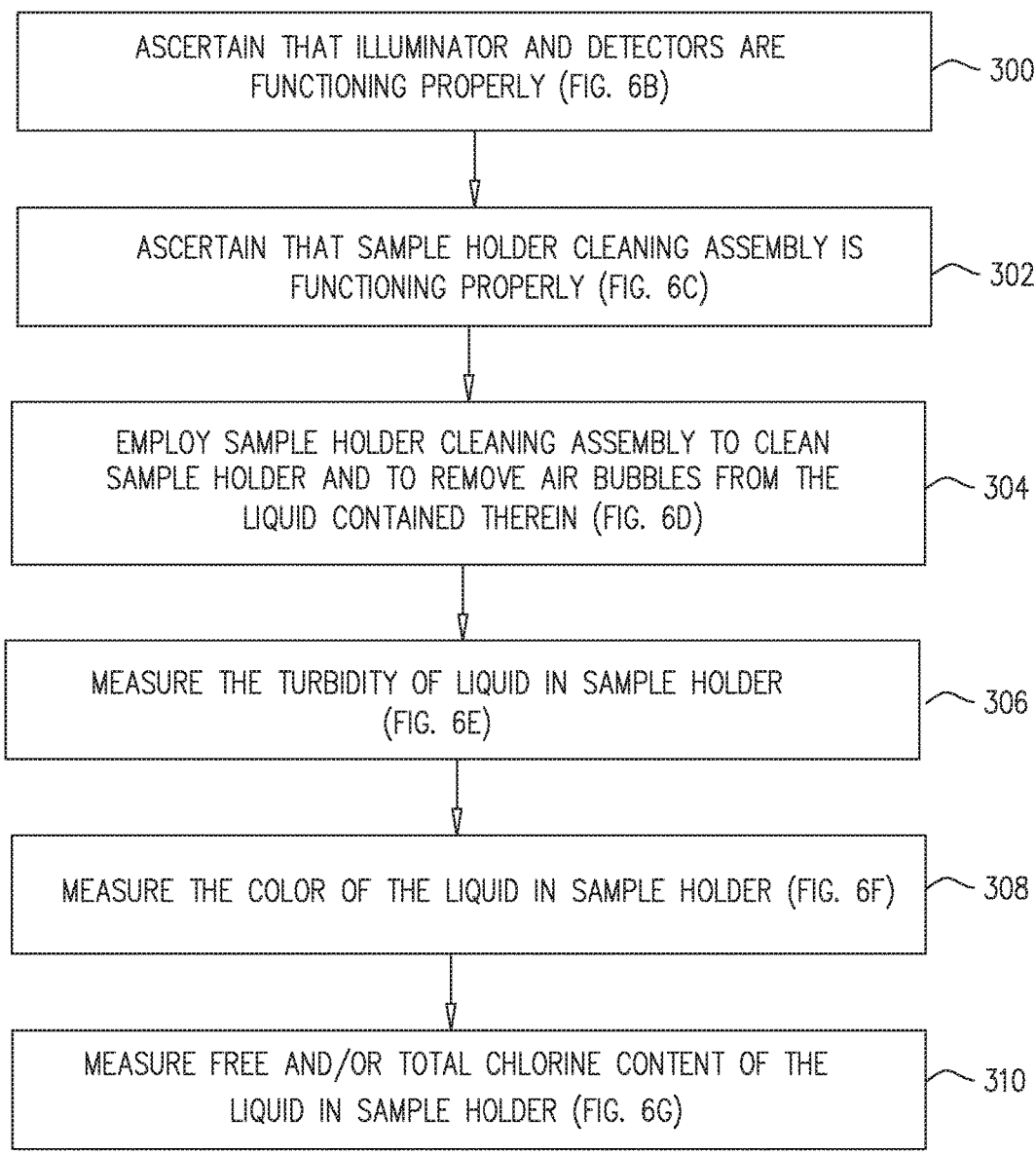

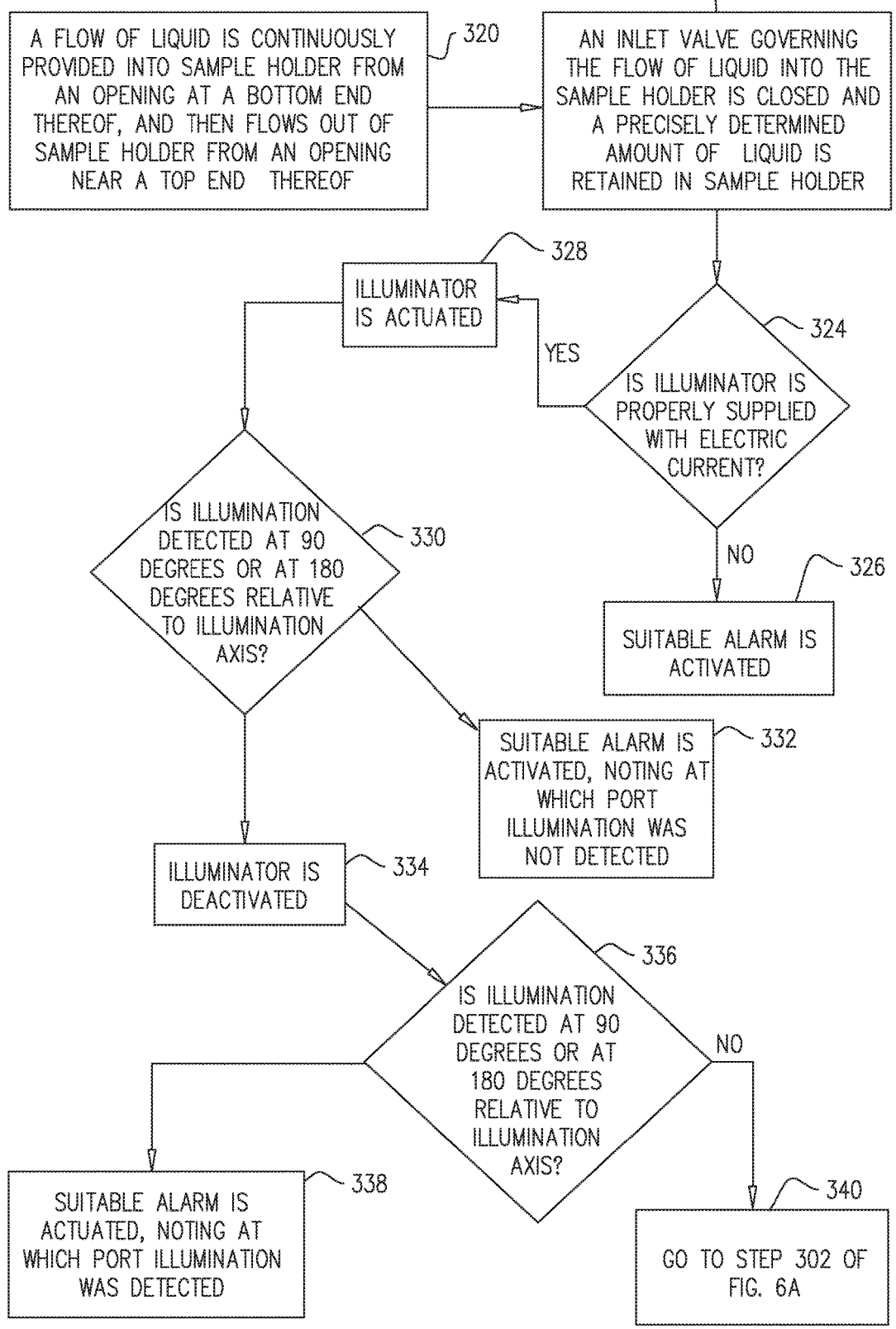

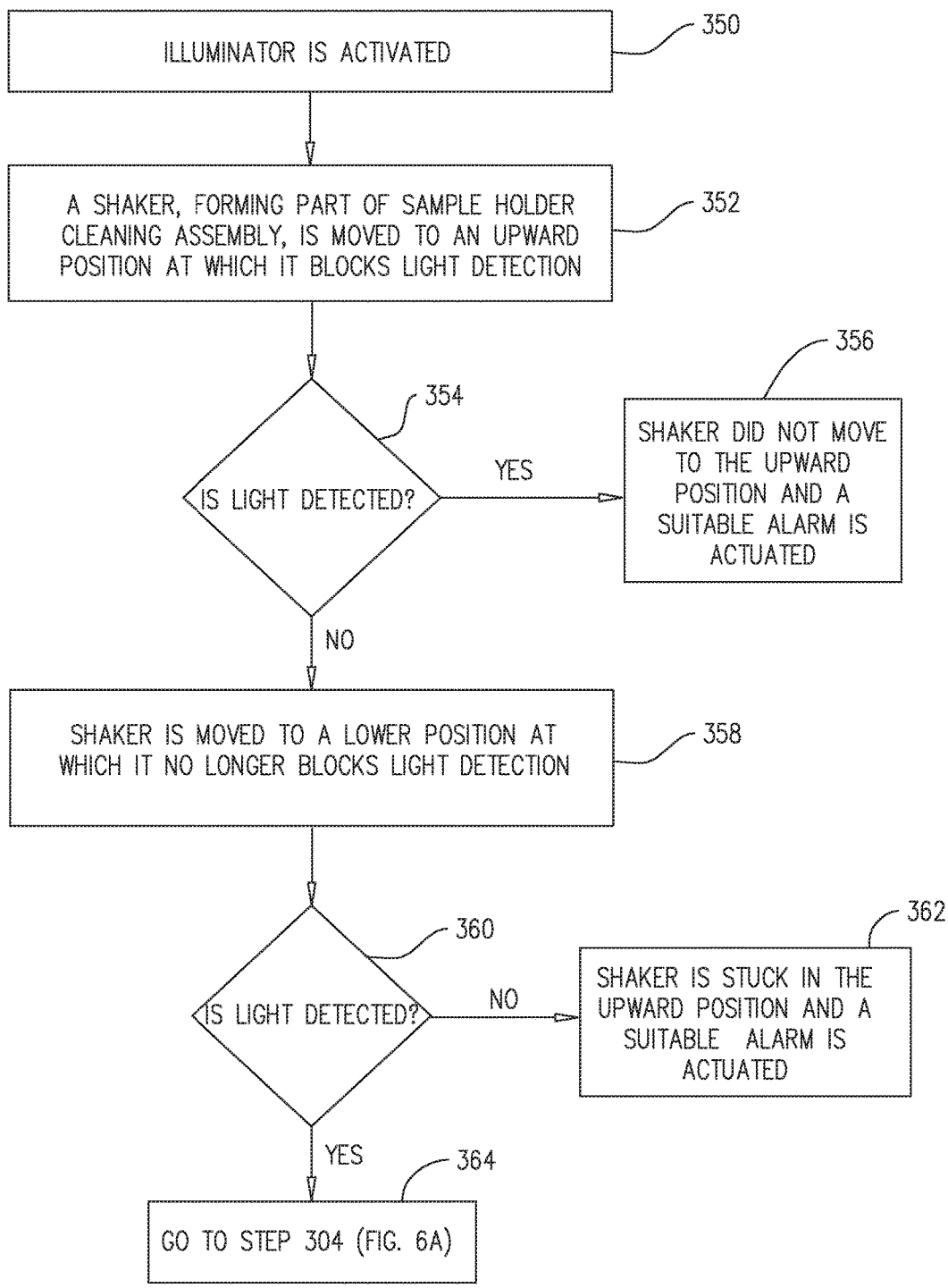

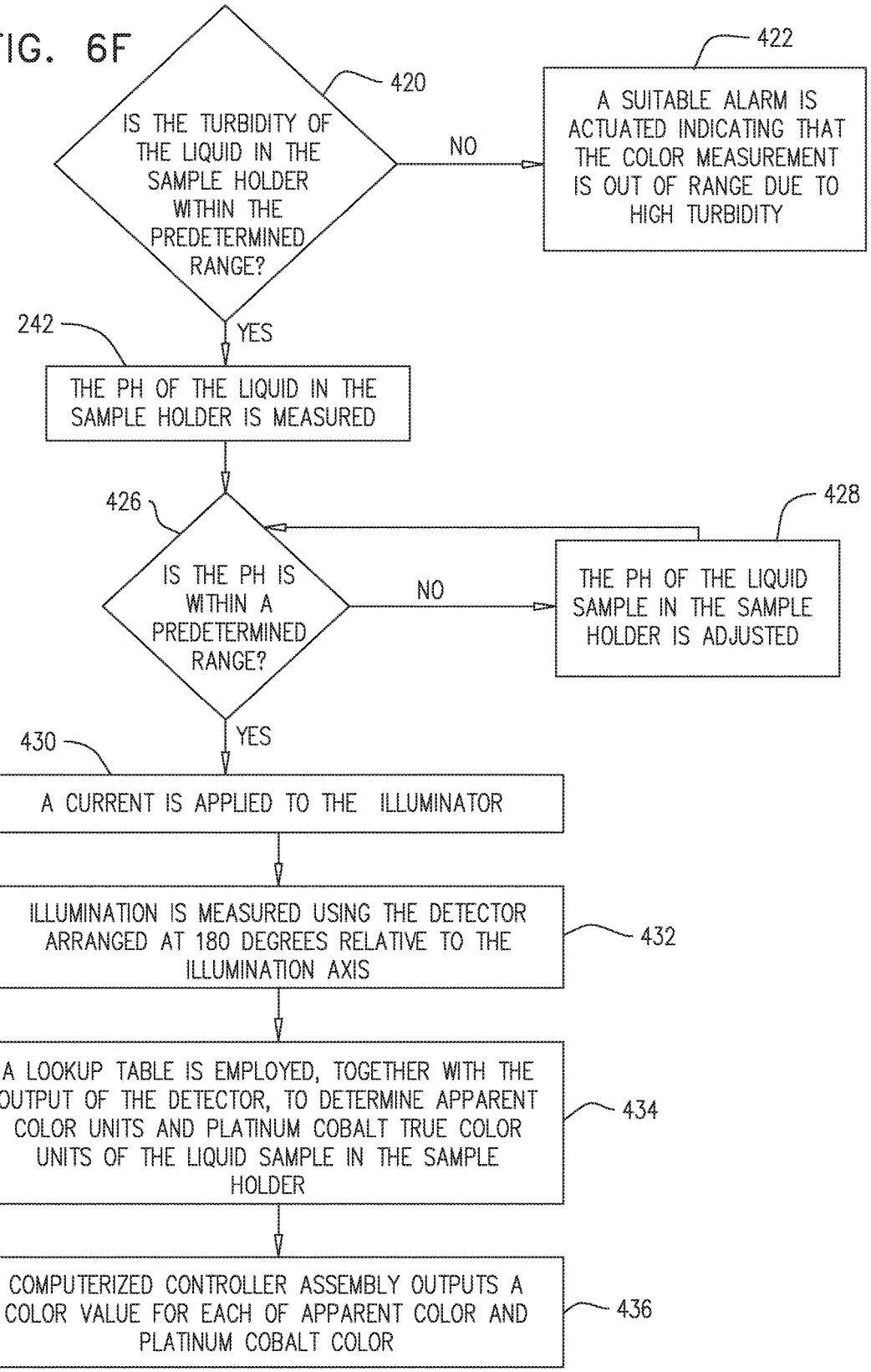

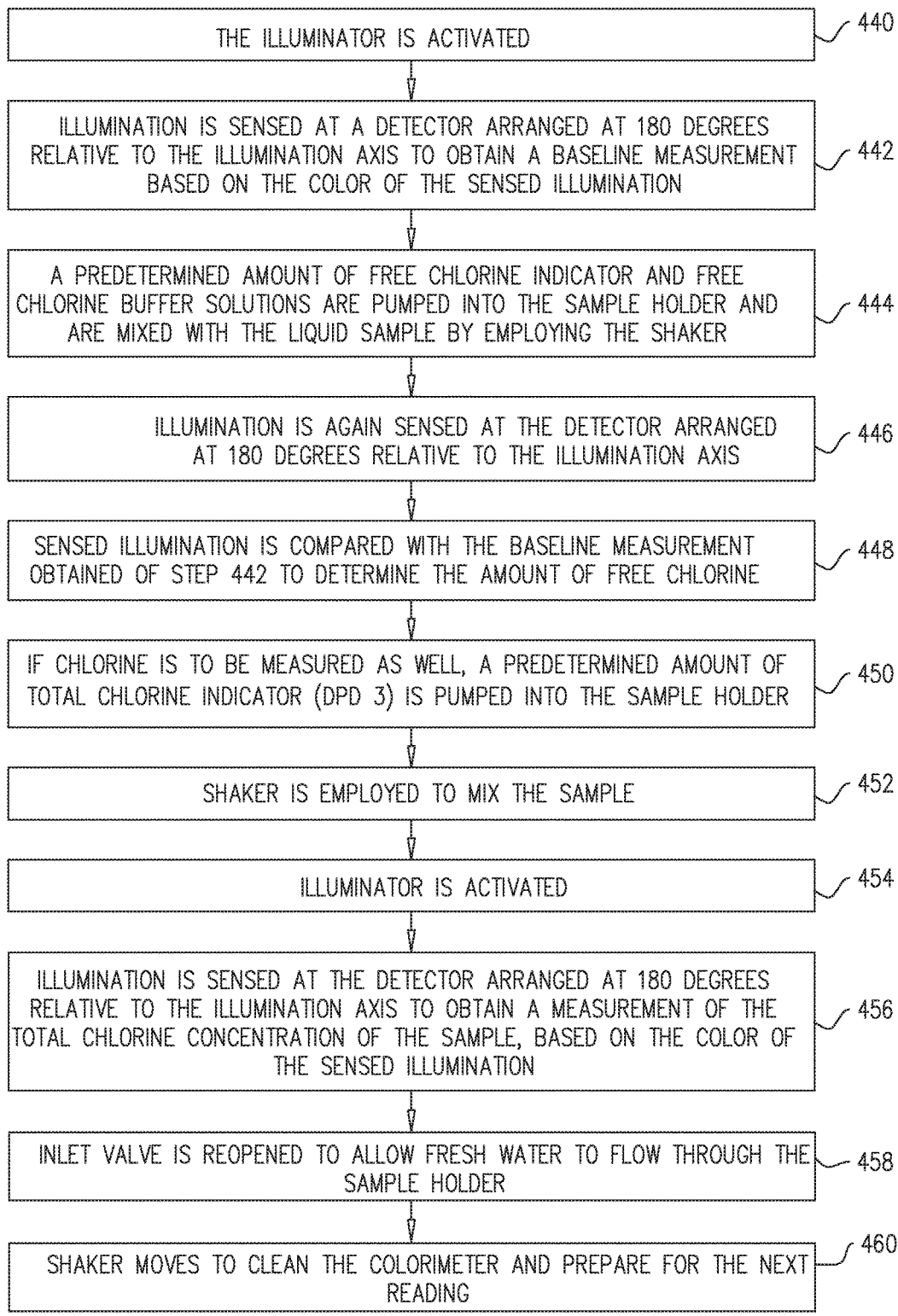

SYSTEM AND METHOD FOR SIMULTANEOUS MEASUREMENT OF TURBIDITY, COLOR AND CHLORINE CONTENT OF A SAMPLE OF A LIQUID

REFERENCE TO RELATED APPLICATIONS

Reference is made to U.S. Provisional Patent Application Ser. No. 61/830,271, filed Jun. 3, 2013 and entitled "APPARATUS FOR MEASURING TURBIDITY, COLOR AND CHLORINE IN A LIQUID", the disclosure of which is hereby incorporated by reference and priority of which is hereby claimed pursuant to 37 CFR 1.78(a) (4) and (5)(i).

Reference is also made to U.S. Pat. No. 7,662,342 of the present assignee, the disclosure of which is hereby incorporated by reference.

FIELD OF THE INVENTION

The present invention relates generally to automated measurement of turbidity and/or color and/or free chlorine and/or total chlorine of liquids.

BACKGROUND OF THE INVENTION

Various types of equipment are known for measurement of turbidity, color and chlorine content of liquids. However, existing equipment is typically not capable of simultaneously or near simultaneously measuring turbidity, color and chlorine content of a single sample of liquid, which would obviate the need to retrieve several samples of the liquid and analyze them separately.

SUMMARY OF THE INVENTION

The present invention seeks to provide a system and method for simultaneous or near simultaneous measurement of at least two of turbidity, color and chlorine content of a sample of a liquid.

There is thus provided in accordance with a preferred embodiment of the present invention a method for measuring turbidity, chlorine content and color of a liquid, the method including retaining, from a continuous flow of the liquid, a sample volume of the liquid, and at least nearly simultaneously executing at least two of detecting illumination from the sample volume of liquid by at least a first detector operable for detecting illumination from the sample volume of liquid at a 90-degree angle with respect to an illumination beam generated by an illuminator and impinging on the sample volume of liquid, thereby measuring a turbidity of the sample volume of liquid, detecting illumination from the sample volume of liquid by at least a second detector operable for detecting illumination from the sample volume of liquid at a 180-degree angle with respect to the illumination beam, thereby measuring a color of the sample volume of liquid, and detecting illumination from the sample volume of liquid by the at least second detector, thereby measuring a chlorine content of the sample volume of liquid.

Preferably, the method also includes ascertaining that the illuminator operable to generate the illumination beam is functioning properly. Preferably, the method also includes ascertaining that the at least first detector and at least second detector are functioning properly. Preferably, the method also includes ascertaining that a cleaning assembly of a holder of the volume of liquid is functioning properly.

Preferably, the method also includes employing the cleaning assembly to clean the holder. Preferably, the method also includes employing the cleaning assembly to remove air bubbles from the sample volume of liquid.

Preferably, ascertaining that the illuminator operable to generate the illumination beam is functioning properly includes ascertaining that the illuminator is provided with suitable electric current.

Preferably, ascertaining that the at least first detector and the at least second detector are functioning properly includes actuating the illuminator and analyzing outputs of the at least first detector and the at least second detector to ascertain whether illumination generated by the illuminator has been detected by both the at least first detector and the at least second detector. Preferably, ascertaining that the at least first detector and the at least second detector are functioning properly also includes deactuating the illuminator and analyzing outputs of the at least first detector and the at least second detector to ascertain whether illumination generated by the illuminator has been detected by either of the at least first detector and the at least second detector.

Preferably, ascertaining that the cleaning assembly is functioning properly includes actuating the illuminator and ascertaining that a shaker element forming part of the cleaning assembly is displaceable between at least a first position in which illumination generated by the illuminator is detected by the at least second detector, and at least a second position in which the illumination beam impinging on the sample volume of liquid is not detected by the at least second detector.

Preferably, employing the cleaning assembly to clean the holder includes retaining, from the continuous flow of the liquid, a cleaning volume of the liquid in the holder, repeatedly displacing the shaker between the first position and second position for a first period of time, releasing the cleaning volume of the liquid from the holder, retaining, from the continuous flow of the liquid, a test volume of the liquid in the holder, actuating the illuminator, and analyzing outputs of the at least first detector and the at least second detector to ascertain whether illumination generated by the illuminator has been detected by both the at least first detector and the at least second detector, and whether the illumination generated by the illuminator.

Preferably, employing the cleaning assembly to remove air bubbles from the sample volume of liquid includes repeatedly displacing the shaker between the first position and second position for a second period of time.

Preferably, detecting the illumination from the sample volume of liquid by the at least the first detector, thereby measuring the turbidity of the sample volume of liquid, includes actuating the illuminator at a first current level, analyzing outputs of the at least first detector and the at least second detector to ascertain whether the intensity of illumination generated by the illuminator at the first current level and detected by the at least first detector and the at least second detector is within a predetermined range of intensity, responsive to ascertaining that the intensity of the illumination generated by the illuminator at the first current level and detected by the at least first detector and the at least second detector is within the predetermined range of intensity, a lookup table is employed to determine the turbidity as a function of the intensity of the illumination at the first current level, responsive to ascertaining that the intensity of the illumination generated by the illuminator at the first current level and detected by the at least first detector and the at least second detector is not within the predetermined range of intensity, actuating the illuminator at a second current which second current level is a function of the first current level, analyzing outputs of the at least first detector and the at least second detector to ascertain whether the intensity of illumination generated by the illuminator at the second current level and detected by the at least first detector and the at least second detector is within the predetermined range of intensity, and responsive to ascertaining that the intensity of the illumination generated by the illuminator at the second current level and detected by the at least first detector and the at least second detector is within the predetermined range of intensity, the lookup table is employed to determine the turbidity as a function of the intensity of the illumination at the second current level. Additionally, responsive to ascertaining that the intensity of the illumination generated by the illuminator at the second current level and detected by the at least first detector and the at least second detector is not within the predetermined range of intensity, analyzing outputs of at least one of a third detector and a fourth detector to ascertain whether the intensity of illumination generated by the illuminator at either of the first current level and the second current level and detected by the at least one of the third detector and the fourth detector is within the predetermined range of intensity, the third detector being operable for detecting illumination from the sample volume of liquid at a 45-degree angle with respect to the illumination beam and the fourth detector being operable for detecting illumination from the sample volume of liquid at a 150-degree angle with respect to the illumination beam, and responsive to ascertaining that the intensity of the illumination generated by the illuminator at either of the first current level and the second current level and detected by at least one of the third detector and the fourth detector is within the predetermined range of intensity, the lookup table is employed to determine the turbidity as a function of the intensity of the illumination.

Preferably, the lookup table is based on a pre-calibrated light intensity/turbidity curve for the first detector, and wherein turbidity values in the lookup table are based on nephelometric analysis.

Preferably, detecting the illumination from the sample volume of liquid by the at least the second detector, thereby measuring the color of the sample volume of liquid, includes ascertaining whether the turbidity of the sample volume of liquid is within a predetermined turbidity range, responsive to ascertaining that the turbidity of the sample volume of liquid is within the predetermined turbidity range, measuring the pH of the liquid, ascertaining whether the pH is within a predetermined pH range, responsive to ascertaining that the pH is not within the predetermined pH range, adjusting the pH of the sample volume of liquid, measuring an adjusted pH of the sample volume of liquid and ascertaining whether the adjusted pH is within the predetermined pH range, responsive to ascertaining that the pH is within the predetermined pH range, actuating the illuminator and obtaining an output of the at least second detector, and employing a color lookup table and the output of the at least second detector to determine apparent color units and platinum cobalt true color units of the sample volume of liquid.

Preferably, the predetermined pH range is between 4 and 10.

Preferably, adjusting the pH of the sample volume of liquid includes employing at least one reagent pump to add at least one of an acid, a base or a buffer reagent to the sample volume of liquid and by employing the shaker to mix the sample volume of liquid while removing bubbles therefrom.

Preferably, the lookup table includes apparent color units between 400 nm-700 nm and platinum cobalt true color units between 450-465 nm as a function of turbidity range between 0 ntu-1000 ntu and pH between 4-10.

Preferably, detecting the illumination from the sample volume of liquid by the at least second detector, thereby measuring the chlorine content of the sample volume of liquid, includes actuating the illuminator and obtaining a baseline output of the at least second detector, pumping a predetermined amount of a free chlorine indicator and a free chlorine buffer solutions into sample volume of liquid and mixing the sample volume of liquid by employing the shaker, obtaining a first test output of the at least second detector, and comparing the first test output to the baseline output to determine an amount of free chlorine in the volume of liquid.

Preferably, detecting the illumination from the sample volume of liquid by the at least second detector, thereby measuring the chlorine content of the sample volume of liquid, also includes pumping a predetermined amount of a total chlorine indicator solution into sample volume of liquid and mixing the sample volume of liquid by employing the shaker, obtaining a second test output of the at least second detector, and comparing the second test output to the baseline output to determine an amount of total chlorine in the volume of liquid.

Preferably, the free chlorine indicator is DPD 1. Preferably, the total chlorine indicator is DPD 3.

Alternatively, detecting the illumination from the sample volume of liquid by the at least second detector, thereby measuring the chlorine content of the sample volume of liquid comprises actuating the illuminator and obtaining a baseline output of the at least second detector, pumping a predetermined amount of a total chlorine indicator solution into sample volume of liquid and mixing the sample volume of liquid by employing the shaker, obtaining a test output of the at least second detector, and comparing the test output to the baseline output to determine an amount of total chlorine in the volume of liquid. Preferably, the total chlorine indicator is DPD 4.

There is also provided in accordance with another preferred embodiment of the present invention a system for measuring turbidity, chlorine content and color of a liquid, the system including a sample holder operable for retaining, from a continuous flow of the liquid, a sample volume of the liquid, at least a first detector operable for detecting illumination from the sample volume of liquid at a 90-degree angle with respect to an illumination beam generated by an illuminator and impinging on the sample volume of liquid, thereby measuring a turbidity of the sample volume of liquid, and at least a second detector operable for detecting illumination from the sample volume of liquid at a 180-degree angle with respect to the illumination beam, thereby measuring a color of the sample volume of liquid and thereby measuring a chlorine content of the sample volume of liquid.

Preferably, the system also includes illumination beam functionality ascertaining functionality operable for ascertaining that the illuminator is operable to properly generate the illumination beam. Preferably, the system also includes detector functionality ascertaining functionality operable for ascertaining that the at least first detector and the at least second detector are functioning properly.

Preferably, the system also includes a holder cleaning assembly operable for cleaning the sample holder. Preferably, the system also includes holder cleaning assembly functionality ascertaining functionality operable for ascertaining that the cleaning assembly is functioning properly. Preferably, the holder cleaning assembly is also operable for removing air bubbles from the sample volume of liquid.

Preferably, ascertaining that the illuminator is operable to properly generate the illumination beam includes ascertaining that the illuminator is provided with suitable electric current.

Preferably, ascertaining that the at least first detector and the at least second detector are functioning properly includes actuating the illuminator, and analyzing outputs of the at least first detector and the at least second detector to ascertain whether illumination generated by the illuminator has been detected by both the at least first detector and the at least second detector.

Preferably, ascertaining that the at least first detector and the at least second detector are functioning properly also includes deactuating the illuminator, and analyzing outputs of the at least first detector and the at least second detector to ascertain whether illumination generated by the illuminator has been detected by either of the at least first detector and the at least second detector.

Preferably, the cleaning assembly includes a shaker. Preferably, ascertaining that the cleaning assembly is functioning properly includes actuating the illuminator, and ascertaining that the shaker element forming part of the cleaning assembly is displaceable between at least a first position in which illumination generated by the illuminator is detected by the at least second detector, and at least a second position in which the illumination beam impinging on the sample volume of liquid is not detected by the at least second detector.

Preferably, employing the cleaning assembly to clean the holder includes retaining, from the continuous flow of the liquid, a cleaning volume of the liquid in the holder, repeatedly displacing the shaker between the first position and second position for a first period of time, releasing the cleaning volume of the liquid from the holder, retaining, from the continuous flow of the liquid, a test volume of the liquid in the holder, actuating the illuminator, and analyzing outputs of the at least first detector and the at least second detector to ascertain whether illumination generated by the illuminator has been detected by both the at least first detector and the at least second detector, and whether the illumination generated by the illuminator.

Preferably, employing the cleaning assembly to remove air bubbles from the sample volume of liquid includes repeatedly displacing the shaker between the first position and second position for a second period of time.

Preferably, the system also includes at least a third detector operable for detecting illumination from the sample volume of liquid at a 45-degree angle with respect to the illumination beam and at least a fourth detector operable for detecting illumination from the sample volume of liquid at a 150-degree angle with respect to the illumination beam.

Preferably, measuring the turbidity of the sample volume of liquid, includes actuating the illuminator at a first current level, analyzing outputs of the at least first detector and the at least second detector to ascertain whether the intensity of illumination generated by the illuminator at the first current level and detected by the at least first detector and the at least second detector is within a predetermined range of intensity, responsive to ascertaining that the intensity of the illumination generated by the illuminator at the first current level and detected by the at least first detector and the at least second detector is within the predetermined range of intensity, a lookup table is employed to determine the turbidity as a function of the intensity of the illumination at the first current level, responsive to ascertaining that the intensity of the illumination generated by the illuminator at the first current level and detected by the at least first detector and the at least second detector is not within the predetermined range of intensity, actuating the illuminator at a second current which second current level is a function of the first current level, analyzing outputs of the at least first detector and the at least second detector to ascertain whether the intensity of illumination generated by the illuminator at the second current level and detected by the at least first detector and the at least second detector is within the predetermined range of intensity, and responsive to ascertaining that the intensity of the illumination generated by the illuminator at the second current level and detected by the at least first detector and the at least second detector is within the predetermined range of intensity, the lookup table is employed to determine the turbidity as a function of the intensity of the illumination at the second current level.

Additionally, responsive to ascertaining that the intensity of the illumination generated by the illuminator at the second current level and detected by the at least first detector and the at least second detector is not within the predetermined range of intensity, analyzing outputs of at least one of a third detector and a fourth detector to ascertain whether the intensity of illumination generated by the illuminator at either of the first current level and the second current level and detected by the at least one of the third detector and the fourth detector is within the predetermined range of intensity, the third detector being operable for detecting illumination from the sample volume of liquid at a 45-degree angle with respect to the illumination beam and the fourth detector being operable for detecting illumination from the sample volume of liquid at a 150-degree angle with respect to the illumination beam, and responsive to ascertaining that the intensity of the illumination generated by the illuminator at either of the first current level and the second current level and detected by at least one of the third detector and the fourth detector is within the predetermined range of intensity, the lookup table is employed to determine the turbidity as a function of the intensity of the illumination.

Preferably, the lookup table is based on a pre-calibrated light intensity/turbidity curve for the first detector, and wherein turbidity values in the lookup table are based on nephelometric analysis.

Preferably, measuring the color of the sample volume of liquid, includes ascertaining whether the turbidity of the sample volume of liquid is within a predetermined turbidity range, responsive to ascertaining that the turbidity of the sample volume of liquid is within the predetermined turbidity range, measuring the pH of the liquid, ascertaining whether the pH is within a predetermined pH range, responsive to ascertaining that the pH is not within the predetermined pH range, adjusting the pH of the sample volume of liquid, measuring an adjusted pH of the sample volume of liquid and ascertaining whether the adjusted pH is within the predetermined pH range, responsive to ascertaining that the pH is within the predetermined pH range, actuating the illuminator and obtaining an output of the at least second detector, and employing a color lookup table and the output of the at least second detector to determine apparent color units and platinum cobalt true color units of the sample volume of liquid. Preferably, the predetermined pH range is between 4 and 10. Preferably, adjusting the pH of the sample volume of liquid includes employing at least one reagent pump to add at least one of an acid, a base or a buffer reagent to the sample volume of liquid and by employing the shaker to mix the sample volume of liquid while removing bubbles therefrom.

Preferably, the lookup table includes apparent color units between 400 nm-700 nm and platinum cobalt true color units between 450-465 nm as a function of turbidity range between 0 ntu-1000 ntu and pH between 4-10.

Preferably, measuring the chlorine content of the sample volume of liquid includes actuating the illuminator and obtaining a baseline output of the at least second detector, pumping a predetermined amount of a free chlorine indicator and a free chlorine buffer solutions into sample volume of liquid and mixing the sample volume of liquid by employing the shaker, obtaining a first test output of the at least second detector, and comparing the first test output to the baseline output to determine an amount of free chlorine in the volume of liquid.

Preferably, measuring the chlorine content of the sample volume of liquid also includes pumping a predetermined amount of a total chlorine indicator solution into sample volume of liquid and mixing the sample volume of liquid by employing the shaker, obtaining a second test output of the at least second detector, and comparing the second test output to the baseline output to determine an amount of total chlorine in the volume of liquid.

Preferably, the free chlorine indicator is DPD 1. Preferably, the total chlorine indicator is DPD 3.

Alternatively, the measuring the chlorine content of the sample volume of liquid includes actuating the illuminator and obtaining a baseline output of the at least second detector, pumping a predetermined amount of a total chlorine indicator solution into sample volume of liquid and mixing the sample volume of liquid by employing the shaker, obtaining a test output of the at least second detector, and comparing the test output to the baseline output to determine an amount of total chlorine in the volume of liquid. Preferably, the total chlorine indicator is DPD 4.

BRIEF DESCRIPTION OF THE DRAWINGS

The present invention will be understood and appreciated from the following detailed description, taken in conjunction with the drawings in which:

FIG. 3 is a simplified illustration of an illumination and detection assembly, forming part of the CTC measurement module employed in the system of FIG. 1;

FIGS. 4A and 4B are simplified pictorial side view illustrations of a base element forming part of the illumination and detection assembly of FIG. 3;

FIGS. 5A and 5B are simplified pictorial illustrations of a detector assembly forming part of the illumination and detection assembly of FIG. 3; and FIGS. 6A, 6B, 6C, 6D, 6E, 6F and 6G are simplified flowcharts illustrating a preferred mode of operation of the system of FIGS. 1-5B.

DETAILED DESCRIPTION OF A PREFERRED EMBODIMENT

Figure 1:
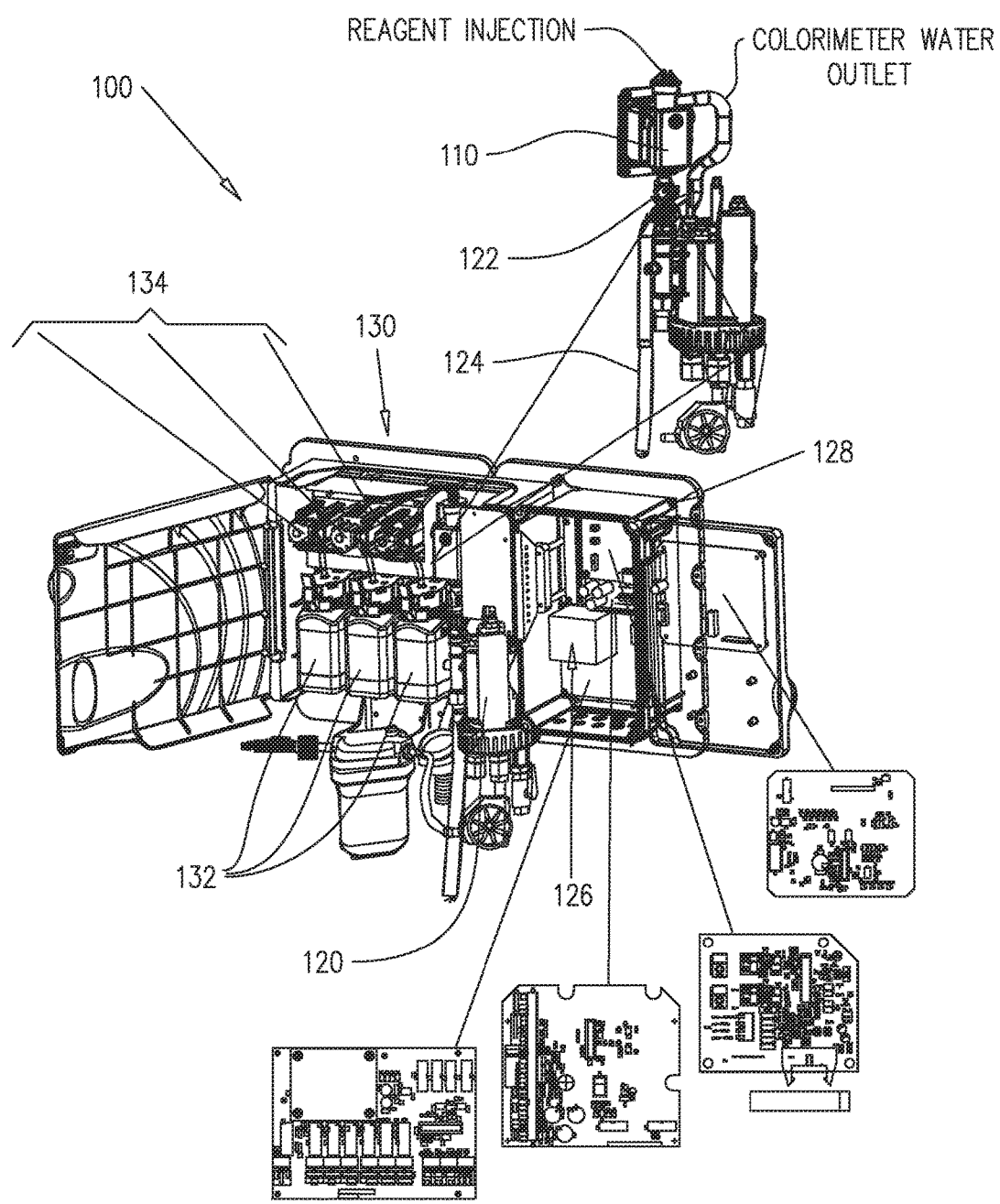
FIG. 1 is a simplified illustration of a color, turbidity and chlorine content (CTC) analysis system constructed and operative in accordance with a preferred embodiment of the present invention.

Reference is now made to FIG. 1, which is a simplified illustration of a color, turbidity and chlorine content (CTC) analysis system 100 constructed and operative in accordance with a preferred embodiment of the present invention. System 100 is preferably operable for simultaneously or nearly simultaneously measuring turbidity, chlorine content and color of a liquid by:

retaining, from a continuous flow of the liquid, a sample volume of the liquid; and at least nearly simultaneously executing at least two of:

detecting illumination from the sample volume of liquid by at least a first detector operable for detecting illumination from the sample volume of liquid at a 90-degree angle with respect to an illumination beam generated by an illuminator and impinging on the sample volume of liquid, thereby measuring a turbidity of the sample volume of liquid;

detecting illumination from the sample volume of liquid by at least a second detector operable for detecting illumination from the sample volume of liquid at a 180-degree angle with respect to the illumination beam, thereby measuring a color of the sample volume of liquid; and detecting illumination from the sample volume of liquid by the at least second detector, thereby measuring a chlorine content of the sample volume of liquid.

As seen in FIG. 1, the CTC analysis system 100 includes a CTC measurement module 110, which is configured to receive samples of liquid to be analyzed from a sampling cell assembly 120, via a solenoid valve 122. CTC measurement module 110 is also configured to output liquid contained therewithin, such as analyzed samples of liquid or liquid used for cleaning the interior of module 110, via a drain pipe 124. Sampling cell assembly 120 may be, for example, a sampling cell assembly commercially available from Blue-I Water Technologies Ltd. of Rosh Ha'ayin, Israel, under Catalog No. 970-210-2120.

The operation of CTC measurement module 110 is preferably controlled by a computerized controller assembly 126, which is typically enclosed in a protective enclosure 128. Enclosure 128 is typically separate from and adjacent to an enclosure 130, which enclosure 130 preferably houses CTC measurement module 110 together with part of sampling cell assembly 120, a multiplicity of reagent containers 132 and a multiplicity of reagent pumps 134. In addition to the specific operation of CTC measurement module 110 described hereinbelow, parts of the structure and operation of system 100 are described in U.S. Pat. No. 7,662,342 of the Applicant, the disclosure of which is hereby incorporated by reference.

Figure 2A:
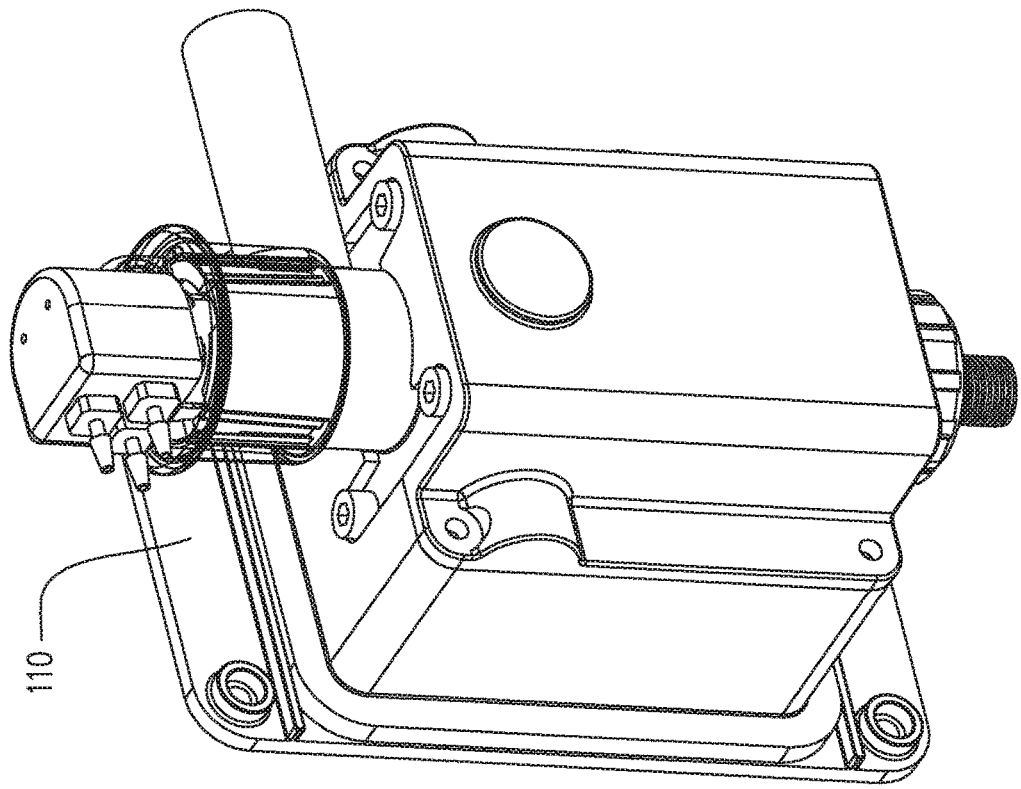
FIGS. 2A & 2B are respective simplified assembled and exploded view illustrations of a CTC measurement module employed in the system of FIG. 1.
Figure 2B:
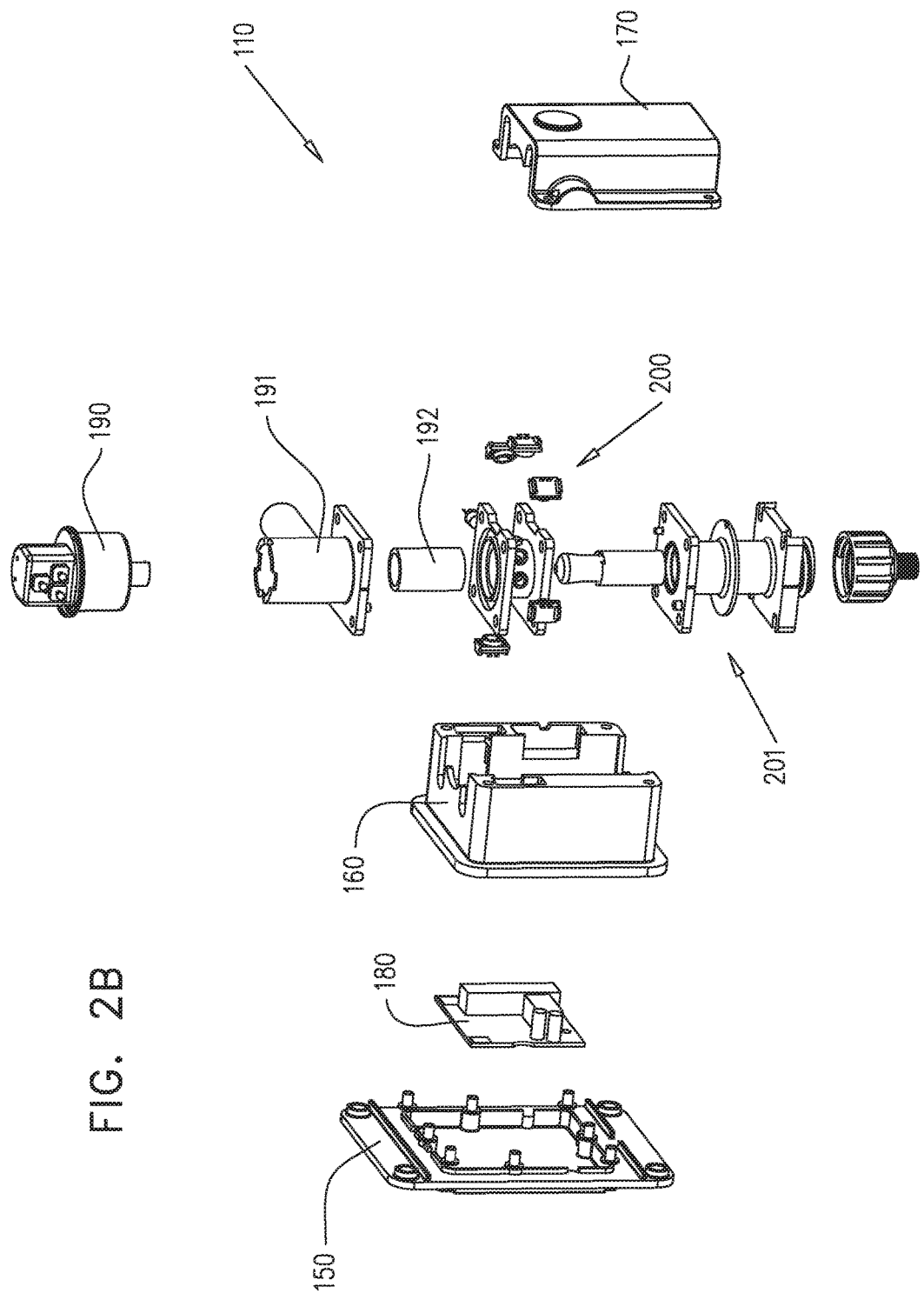

Reference is now made to FIGS. 2A & 2B, which are respective simplified assembled and exploded view illustrations of CTC measurement module 110 employed in the system of FIG. 1. As shown in FIGS. 2A & 2B, CTC measurement module 110 preferably includes a base element 150 such as, for example, a base element commercially available from Blue-I Water Technologies Ltd. of Rosh Ha'ayin, Israel, under Catalog No. 1-COVER-PCB. A housing element 160 is preferably mounted onto base element 150. Housing element 160, may be, for example, a housing element commercially available from Blue-I Water Technologies Ltd. of Rosh Ha'ayin, Israel, under Catalog No. 970-210-3004. Also preferably mounted onto base element 150 is a light-tight housing element cover 170.

Preferably disposed within a housing defined by base element 150, housing element 160 and housing element cover 170 is a calibration memory board 180, which preferably includes a suitably programmed EPROM, such as an 8K I²C™ commercially available from Microchip Technology of Chandler, Ariz., USA under Catalog No. 24AA08/24LC08B.

Also preferably disposed within the housing defined by base element 150, housing element 160 and housing element cover 170 is an injection module 190, such as an injection module commercially available from Blue-I Water Technologies Ltd. of Rosh Ha'ayin, Israel, under either Catalog No. 970-210-3018 or Catalog No. 970-210-3019. Injection module 190 is preferably supported upon a measuring head 191, such as a measuring head commercially available from Blue-I Water Technologies Ltd. of Rosh Ha'ayin, Israel, under Catalog No. 970-210-3014.

Injection module 190 is preferably operable for injecting reagents into a sample of liquid which is held in a transparent glass sample holder 192, such as a glass sample holder commercially available from Blue-I Water Technologies Ltd. of Rosh Ha'ayin, Israel, under Catalog No 970-210-3017.

An illumination and detection assembly 200 is preferably arranged to support sample holder 192 and to be in optical communication therewith, as described hereinbelow in detail with reference to FIGS. 3-5B.

Preferably associated with sample holder 192 is a sample holder cleaning assembly 201, such as a cleaning assembly commercially available from Blue-I Water Technologies Ltd. of Rosh Ha'ayin, Israel, under Catalog Nos. 970-210-3101 and 970-210-3204.

Reference is now made to FIG. 3, which is a simplified exploded view illustration of illumination and detection assembly 200, and to FIGS. 4A & 4B, which are simplified opposite side view illustrations of a base element 202 thereof. As seen in FIGS. 3, 4A & 4B, illumination and detection assembly 200 preferably includes a base element 202, preferably formed of plastic by injection molding. Base element 202 preferably includes respective top and bottom plate portions 204 and 206 which are preferably joined by a generally cylindrical portion 208. An illumination conduit 210 preferably intersects cylindrical portion 208. An illuminator port 212 is preferably formed at an end of illumination conduit 210.

A bore 214 is preferably formed through top plate portion 204, generally cylindrical portion 208 and bottom plate portion 206 of base element 202, along an axis 216 which is generally perpendicular to a top surface of top plate portion 204. Bore 214 is preferably configured to receive sample holder 192.

As seen particularly in FIG. 4A, generally cylindrical portion 208 is formed with multiple detector mounting ports arranged for light-tight mounting of light detector assemblies thereon. The detector mounting ports preferably include a first detector mounting port 220 located perpendicular to an illumination axis 222 defined by illumination conduit 210, and a second detector mounting port 224 located opposite illuminator port 212 along illumination axis 222. Additional optional detector mounting ports 226 and 228 are preferably respectively arranged at 45 and 150 degree angles relative to illumination axis 222.

As seen particularly in FIG. 4B, an illumination test detector port 230 is preferably provided on illumination conduit 210, perpendicular to illumination axis 222.

Detector assemblies 240 are preferably removably mounted onto each of detector mounting ports 220, 224, 226, 228 and 230 in a light-tight manner. An LED illuminator 250, such as a YZ-W5S20N LED lamp, commercially available from YolDal Ltd. of Zhonghe City Taiwan, is preferably removably mounted onto illuminator port 212 of illumination conduit 210. It is appreciated that illuminator 250 is preferably configured for illuminating an interior volume of bore 214, thereby illuminating liquid contained within transparent glass sample holder 192. Detector assemblies 240 are preferably operable for detecting illumination generated by illuminator 250 and which traverses liquid contained within transparent glass sample holder 192.

Reference is now made to FIGS. 5A and 5B, which are simplified pictorial illustrations of detector assembly 240 forming part of illumination and detection assembly 200 of FIG. 3. As shown in FIGS. 5A & 5B, detector assembly 240 preferably includes a detector 260, such as a detector commercially available from Texas Advanced Optoelectronic Solutions Inc. of Plano, Tex., under either of catalog numbers TCS 3403 or TCS 3413, and a detector mount 262. Detector mount 262 preferably includes a port connector portion 264, which is configured for tight engagement with any of ports 220, 224, 226, 228 and 230 in a light-tight manner. Detector mount 262 preferably also includes a detector mounting portion 266, which is configured to retain detector 260 to port connector portion 264 in a light-tight manner.

It is appreciated that detectors 260 are operative both as an ambient light sensor and an RGB color sensor. It is also appreciated that additionally or alternatively, detectors 260 may be operative to detect a specific wavelength, or may be fitted with a filter operative to filter only a specific wavelength.

Figure 6D:
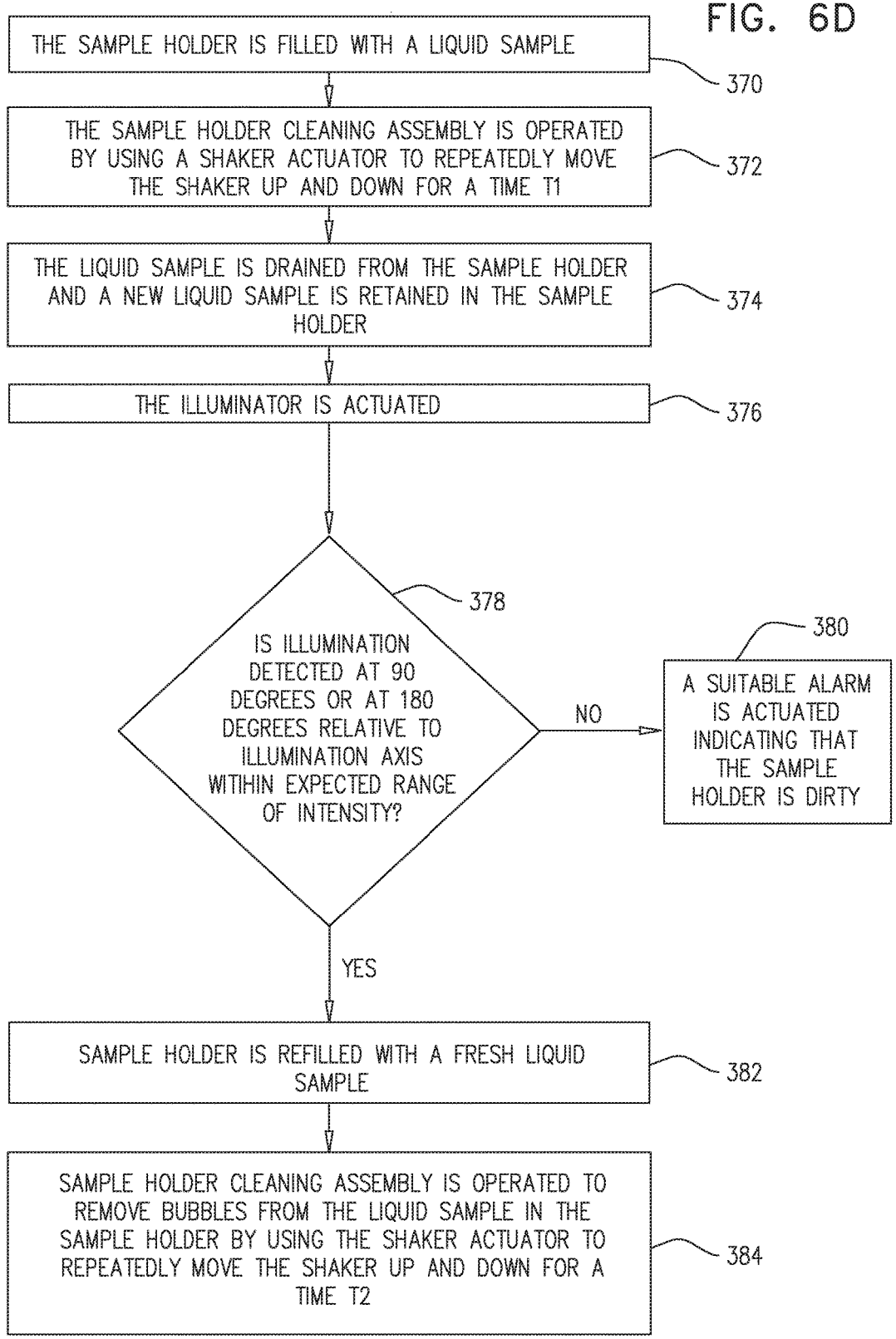

Reference is now made to FIGS. 6A, 6B, 6C, 6D, 6E, 6F and 6G, which are simplified flowcharts illustrating a preferred mode of operation of system 100 of FIGS. 1-5B. As seen in FIG. 6A, the operation of system 100 preferably includes the following principal steps:

ascertaining that illuminator 250 and detectors 240 are functioning properly, as will be described in detail hereinbelow with reference to FIG. 6B (300);

ascertaining that sample holder cleaning assembly 201 is functioning properly, as will be described in detail hereinbelow with reference to FIG. 6C (302);

employing sample holder cleaning assembly 201 to clean sample holder 192 and to remove air bubbles from the liquid contained therein, as will be described in detail hereinbelow with reference to FIG. 6D (304);

measuring the turbidity of liquid in sample holder 192, as will be described in detail hereinbelow with reference to FIG. 6E (306);

measuring the color of the liquid in sample holder 192, the turbidity of which was measured in step 306, as will be described in detail hereinbelow with reference to FIG. 6F (308); and/or measuring free and/or total chlorine content of the liquid in sample holder 192, the turbidity of which was measured in step 306, as will be described in detail hereinbelow with reference to FIG. 6G (310).

Reference is now made to FIG. 6B, which describes step 300 (FIG. 6A), which includes ascertaining that illuminator 250 and detectors 240 are functioning properly.

As shown in step 320 of FIG. 6B, a flow of liquid is generally continuously provided into sample holder 192 from an opening at a bottom end thereof, and then flows out of sample holder 192 from an opening near a top end thereof. As further shown in step 322, intermittently, and preferably periodically, an inlet valve governing the flow of liquid into the sample holder 192 is closed and a precisely determined amount of liquid is retained in sample holder 192. The liquid is typically drinking water, however it may be any other liquid for which measuring of any of turbidity, color and chlorine content is desired.

As yet further shown in step 324, the system ascertains that illuminator 250 is properly supplied with electric current. Responsive to ascertaining that illuminator 250 is not properly supplied with electric current, a suitable alarm is activated (326). Responsive to ascertaining that illuminator 250 is properly supplied with electric current, illuminator 250 is actuated (328) and the outputs of detectors 260 mounted on ports 220 and 224, arranged at 90 degrees and 180 degrees respectively relative to illumination axis 222, are received and analyzed to ascertain whether illumination has been detected (330). Failure to detect illumination at either one of detectors 260 mounted on ports 220 and 224 causes a suitable alarm to be activated, noting at which of ports 220 and 224 illumination was not detected (332).

Alternatively or additionally, the output of detector 260 at port 230 is also received and analyzed. Failure to detect illumination at this detector preferably also causes a suitable alarm to be activated.

If detectors 260 mounted on both ports 220 and 224 detect illumination, illuminator 250 is deactivated (334) and the outputs of detectors 260 at ports 220 and 224 are again received and analyzed to ascertain whether illumination has been detected, thereby ascertaining light tightness of the of the illumination and detection assembly of FIG. 3 (336). If light is detected, a suitable alarm is actuated, noting at which of ports 220 and 224 illumination was detected (338). If no light is detected, the process continues with step 302 of FIG. 6A (340).

Reference is now made to FIG. 6C, which describes step 302 (FIG. 6A), which includes ascertaining that sample holder cleaning assembly 201 is functioning properly.

As shown in FIG. 6C, illuminator 250 is initially activated (350). While illuminator 250 is activated, a shaker, forming part of sample holder cleaning assembly 201, is moved to an upward position at which it blocks light detection by detector 260 at port 224 (352). Detection of light at this stage by detector 260 at port 224 (354) is an indication that the shaker did not move to the upward position and a suitable alarm is actuated (356).

If no light is detected at this stage by detector 260 at port 224, the shaker is then moved to a lower position at which it no longer blocks light detection by detector 260 at port 224 (358). No detection of light at this stage by detector 260 at port 224 (360) is an indication that the shaker is stuck in the upward position and a suitable alarm is actuated (362). If light is detected at this stage by detector 260 at port 224, the process continues with step 304 of FIG. 6A (364).

Reference is now made to FIG. 6D, which describes step 304 (FIG. 6A), which includes employing sample holder cleaning assembly 201 to clean sample holder 192 and to remove air bubbles from the liquid contained therein.

As shown in FIG. 6D, once sample holder 192 is filled with a liquid sample (370), sample holder cleaning assembly 201 is operated by using a shaker actuator to repeatedly move the shaker up and down for a time T1 (372). The liquid sample is then drained from the sample holder and a new liquid sample is retained in the sample holder (374).

Thereafter, illuminator 250 is actuated (376) and the outputs of detectors 260 mounted on ports 220 and 224, arranged at 90 degrees and 180 degrees respectively relative to illumination axis 222, are received and analyzed to ascertain whether illumination has been detected (378). Failure to detect illumination at either of detectors 260 mounted on ports 220 and 224, or detection of illumination at either of detectors 260 mounted on ports 220 and 224 which is outside an expected range of intensity, a suitable alarm is actuated indicating that the sample holder 192 is dirty (380). If illumination detected at both detectors 260 mounted on ports 220 and 224 is within the expected range of intensity, sample holder 192 is refilled with a fresh liquid sample (382) and sample holder cleaning assembly 201 is operated to remove bubbles from the liquid sample in the sample holder 192 by using the shaker actuator to repeatedly move the shaker up and down for a time T2 (384).

Figure 6E:
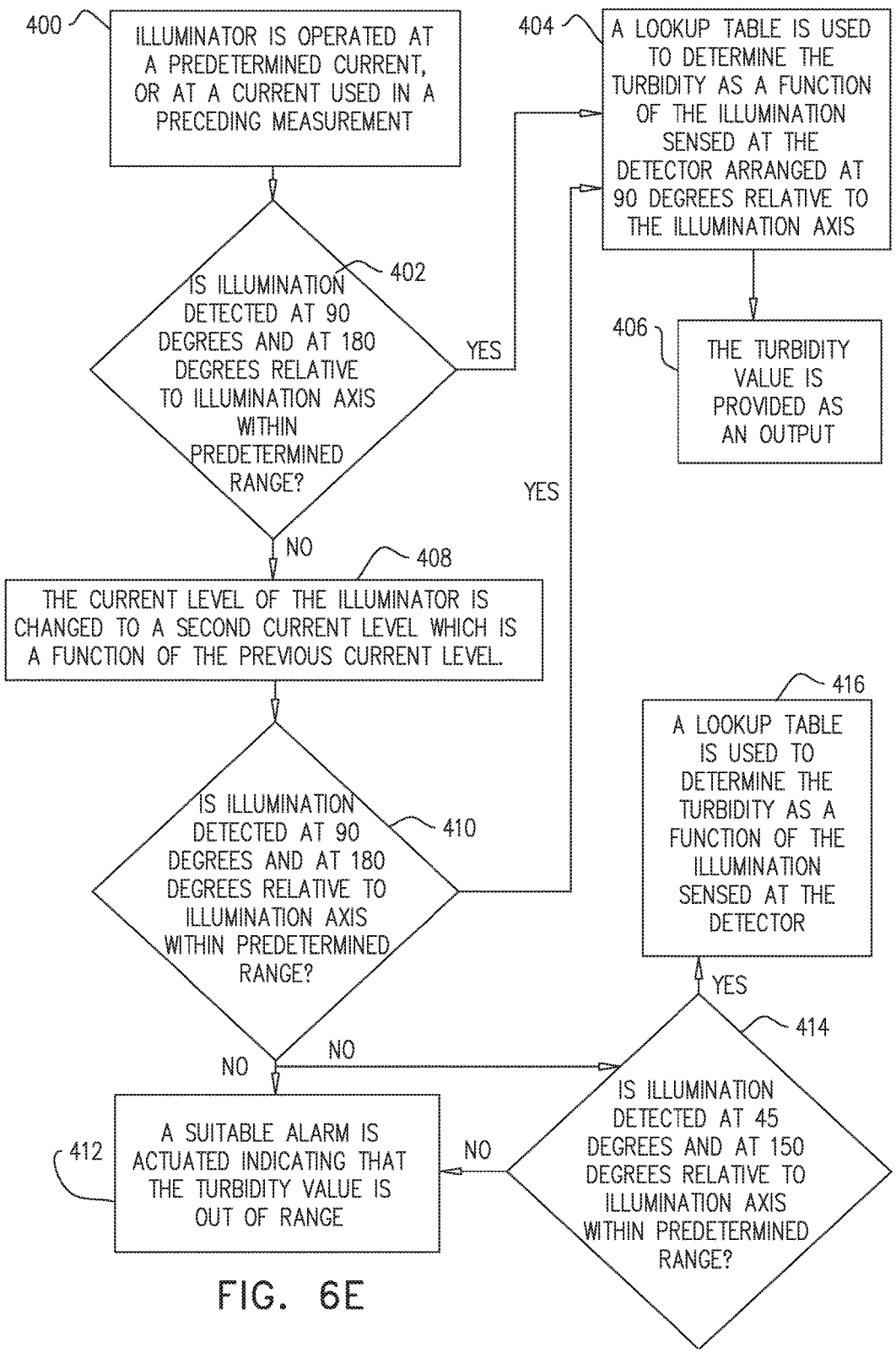

Reference is now made to FIG. 6E, which describes step 306 (FIG. 6A), which includes measuring the turbidity of liquid in sample holder 192.

To measure the turbidity of the liquid in sample holder 192, the illuminator 250 is initially operated at a predetermined current, or at a current used in a preceding measurement (400). The outputs of detectors 260 mounted on ports 220 and 224 arranged at 90 degrees and 180 degrees respectively relative to illumination axis 222 are received and analyzed to ascertain whether the illumination detected at detectors 260 mounted on ports 220 and 224 is within a predetermined range of intensity (402).

Responsive to ascertaining that the intensity of the illumination detected at detectors 260 at ports 220 and 224 is within a predetermined range of intensity, a lookup table is used to determine the turbidity as a function of the intensity of the illumination detected at detector 260 mounted on port 220, arranged at 90 degrees relative to illumination axis 220 (404), and the turbidity value is provided as an output (406). The lookup table is preferably based on a pre-calibrated light intensity/turbidity curve for detector 260 at port 220 arranged at 90 degrees relative to illumination axis 220. It is appreciated that the turbidity values are based on nephelometric analysis.

Responsive to ascertaining that the intensity of the illumination detected at detectors 260 at ports 220 and 224 is not within the predetermined range of intensity, the current level of illuminator 250 is changed to a second current level (408), which second current level is typically a function of the previous current level. Thereafter, the outputs of detectors 260 mounted on ports 220 and 224 arranged at 90 degrees and 180 degrees respectively relative to illumination axis 222 are again received and analyzed to ascertain whether the illumination detected at detectors 260 mounted on ports 220 and 224 are within the predetermined range of intensity (410). Responsive to ascertaining that the illumination detected at detectors 260 at ports 220 and 224 is within the predetermined range of intensity, a lookup table is used to determine the turbidity as a function of the intensity of the illumination detected at detector 260 mounted on port 220, arranged at 90 degrees relative to illumination axis 220 (404), and the turbidity value is provided as an output (406).

Responsive to ascertaining that the intensity of the illumination detected at detectors 260 mounted on ports 220 and 224 is still not within the predetermined range, a suitable alarm is actuated indicating that the turbidity value is out of range (412). Alternatively, the outputs of detectors 260 at port 226 and/or 228, arranged at 45 degrees and 150 degrees respectively relative to illumination axis 222, are received and analyzed to ascertain whether the illumination detected at detectors 260 mounted on port 226 and/or 228 is within a predetermined range (414). Responsive to ascertaining that the intensity of the illumination detected at detectors 260 mounted on ports 226 and/or 228 is within the predetermined range, a lookup table is used to determine the turbidity as a function of the illumination detected at detector 260 mounted on port 226 or 228 (416). Responsive to ascertaining that the illumination detected at detectors 260 mounted on port 226 and/or 228 are not within the predetermined range, a suitable alarm is actuated indicating that the turbidity value is out of range (412).

Reference is now made to FIG. 6F, which describes step 308 (FIG. 6A), which includes measuring the color of the liquid in sample holder 192, the turbidity of which was measured in step 306. It is appreciated that the color of a liquid typically correlates with the level of contamination of the liquid. For example, drinking water may be colored as a result of contamination by material dissolved in the liquid such as, for example, soil or pipe corrosion.

Initially, the system ascertains whether the turbidity of the liquid in sample holder 192 measured as described in FIG. 6E was within the predetermined range (420). Responsive to ascertaining that the turbidity was not within the predetermined range, a suitable alarm is actuated indicating that the color measurement is out of range due to high turbidity (422).

Responsive to ascertaining that the turbidity was within the predetermined range, the pH of the liquid in sample holder 192 is measured (424) and the system ascertains whether the pH is within a predetermined range, typically a range of 4-10 (426). It is appreciated that the pH of the liquid may be measured before entering sample holder 192.

Responsive to ascertaining that the pH is not within the predetermined range, the pH of the liquid sample in sample holder 192 is adjusted (428). The adjustment of the pH is to within the predetermined range, typically to a value of 7.0 or to any other suitable pH, by employing one of reagent pumps 134 to add one of an acid, base or buffer reagent to the sample and by employing the shaker to mix the liquid sample in sample holder 192 while removing bubbles therefrom. Thereafter, a second pH measurement is performed on the same liquid sample in sample holder 192 to ascertain that the pH is within the predetermined range (426).

Responsive to ascertaining that the pH is within the predetermined range, a current is applied to illuminator 250 (430) and illumination is measured using the detector 260 at port 224, arranged at 180 degrees relative to illumination axis 222 (432). A lookup table is then employed, together with the output of detector 260 at port 224, to determine apparent color units and platinum cobalt true color units of the liquid sample in sample holder 192 (434).

Preferably, the lookup table includes apparent color units (400-700 nm) and platinum cobalt true color units (450-465 nm) as a function of turbidity range (0-1000 ntu) and pH (4-10). The lookup table is used to eliminate the influence of turbidity and pH on the detection and determination of color of the liquid sample. Based on the lookup table, computerized controller assembly 126 determines and outputs a color value for each of apparent color and platinum cobalt color (436).

Reference is now made to FIG. 6G, which describes step 310 (FIG. 6A), which includes measuring free and/or total chlorine content of the liquid in sample holder 192, the turbidity of which was measured in step 306. It is appreciated that the free chlorine content of a liquid typically correlates to the residual disinfecting power of the liquid, and that the total chlorine content of a liquid typically correlates to the overall level of contamination of the liquid.

As seen in FIG. 6G, illuminator 250 is activated (440), and illumination is preferably detected at detector 260 mounted on port 224, arranged at 180 degrees relative to illumination axis 222 (442) to obtain a baseline measurement based on the color of the detected illumination, which baseline measurement will be employed in a subsequent free chlorine measurement. The baseline measurement is used for compensating the subsequent free chlorine measurement for to account for turbid water, colored water and/or dirt in sample holder 192.

Thereafter, a predetermined amount of free chlorine indicator, such as DPD 1, and free chlorine buffer solutions are preferably pumped into sample holder 192 and are mixed with the liquid sample by employing the shaker (444). A chemical reaction between the free chlorine indicator and any free chlorine in the liquid sample (hypochlorous acid+ hypochlorite ions) typically induces a color change, typically from a clear color to red. If no free chlorine is present, no change in color will occur.

Thereafter, illumination is again detected at detector 260 mounted on port 224, arranged at 180 degrees relative to illumination axis 222 (446), which detected illumination is then compared with the baseline measurement obtained in step 442 to determine the amount of free chlorine (448). This value is typically reported in parts per million (ppm) or mg/l.

In a case where total chlorine is to be measured as well, a predetermined amount of total chlorine indicator (DPD 3) is then pumped into sample holder 192 into the liquid sample which already contains the free chlorine indicator and the free chlorine buffer (450). The shaker is then preferably employed to mix the sample (452). A chemical reaction between the total chlorine indicator and any total chlorine typically induces a color change from clear to red to a new shade of red. If no total chlorine is present no change in color will occur.

Thereafter, illuminator 250 is preferably activated once again (454) and illumination is preferably detected at detector 260 mounted on port 224, arranged at 180 degrees relative to illumination axis 222 (456), to obtain a measurement of the total chlorine concentration of the sample, based on the color of the detected illumination.

The inlet valve is then reopened to allow fresh water to flow through sample holder 192 (458) and the shaker moves again to clean the colorimeter and prepare for the next reading (460).

Alternatively, in a case where it is desired to measure the total chlorine, without first measuring free chlorine, illuminator 250 is activated and illumination is preferably detected at detector 260 mounted on port 224, arranged at 180 degrees relative to illumination axis 222, to obtain a baseline measurement based on the color of the detected illumination. Thereafter, a predetermined amount of total chlorine indicator, such as DPD 4, is preferably pumped into sample holder 192 and is mixed with the liquid sample by employing the shaker. Thereafter, illuminator 250 is preferably activated once again and illumination is preferably detected at detector 260 mounted on port 224, which detected illumination is then compared with the baseline measurement to determine the amount of total chlorine.

It will be appreciated by persons skilled in the art that the present invention is not limited to what has been particularly shown and described hereinabove. Rather the scope of the invention includes both combinations and subcombinations of the various features described hereinabove as well as modifications and variations thereof which would occur to persons skilled in the art upon reading the foregoing description and which are not in the prior art.

The invention claimed is:

1. A method for measuring turbidity, chlorine content and color of a liquid, said method comprising:
   retaining, from a continuous flow of said liquid, a sample volume of said liquid; and at least nearly simultaneously executing at least two of:

detecting illumination from said sample volume of liquid by at least a first detector operable for detecting illumination from said sample volume of liquid at a 90-degree angle with respect to an illumination beam generated by an illuminator and impinging on said sample volume of liquid, thereby measuring a turbidity of said sample volume of liquid;

detecting illumination from said sample volume of liquid by at least a second detector operable for detecting illumination from said sample volume of liquid at a 180-degree angle with respect to said illumination beam, thereby measuring a color of said sample volume of liquid; and detecting illumination from said sample volume of liquid by said at least second detector, thereby measuring a chlorine content of said sample volume of liquid;

wherein said detecting said illumination from said sample volume of liquid by said at least said first detector, thereby measuring said turbidity of said sample volume of liquid, comprises;

actuating said illuminator at a first current level;

analyzing outputs of said at least first detector and said at least second detector to ascertain whether the intensity of illumination generated by said illuminator at said first current level and detector by said at least first detector and said at least second detector is within a predetermined range of intensity;

responsive to ascertaining that said intensity of said illumination generated by said illuminator at said first current level and detected by said at least first detector and said at least second detector is within said predetermined range of intensity, a lookup table is employed to determine said turbidity as a function of said intensity of said illumination at said first current level;

responsive to ascertaining that said intensity of said illumination generated by said illuminator at said first current level and detected by said at least first detector and said at least second detector is not within said predetermined range of intensity, actuating said illuminator at a second current which second current level is a function of said first current level;

analyzing outputs of said at least first detector and said at least second detector to ascertain whether the intensity of illumination generated by said illuminator at said second current level and detected by said at least first detector and said at least second detector is within said predetermined range of intensity; and responsive to ascertaining that said intensity of said illumination generated by said illuminator at said second current level and detected by said at least first detector and said at least second detector is within said predetermined range of intensity, said lookup table is employed to determine said turbidity as a function of said intensity of said illumination at said second current level.

2. A method for measuring turbidity, chlorine content and color of a liquid according to claim 1 and also comprising ascertaining that one or more elements are functioning properly, the elements selected from said illuminator, said first detector and said second detector.

3. A method for measuring turbidity, chlorine content and color of a liquid according to claim 1 and also comprising employing a cleaning assembly to clean a holder of said volume of liquid.

4. A method for measuring turbidity, chlorine content and color of a liquid according to claim 3 and also comprising employing said cleaning assembly to remove air bubbles from said sample volume of liquid.

5. A method for measuring turbidity, chlorine content and color of a liquid according to claim 1, and wherein said lookup table is based on a pre-calibrated light intensity/turbidity curve for said first detector, and wherein turbidity values in said lookup table are based on nephelometric analysis.

6. A method for measuring turbidity, chlorine content and color of a liquid according to claim 1, and wherein said detecting said illumination from said sample volume of liquid by said at least said second detector, thereby measuring said color of said sample volume of liquid, comprises: ascertaining whether said turbidity of said sample volume of liquid is within a predetermined turbidity range; responsive to ascertaining that said turbidity of said sample volume of liquid is within said predetermined turbidity range, measuring the pH of said liquid; ascertaining whether said pH is within a predetermined pH range; responsive to ascertaining that said pH is not within said predetermined pH range, adjusting said pH of said sample volume of liquid, measuring an adjusted pH of said sample volume of liquid and ascertaining whether said adjusted pH is within said predetermined pH range;

responsive to ascertaining that said pH is within said predetermined pH range, actuating said illuminator and obtaining an output of said at least second detector; and employing a color lookup table and said output of said at least second detector to determine apparent color units and platinum cobalt true color units of said sample volume of liquid.

7. A method for measuring turbidity, chlorine content and color of a liquid according to claim 1, and wherein said detecting said illumination from said sample volume of liquid by said at least second detector, thereby measuring said chlorine content of said sample volume of liquid comprises;

actuating said illuminator and obtaining a baseline output of said at least second detector;

pumping a predetermined amount of a total chlorine indicator solution into sample volume of liquid and mixing said sample volume of liquid by employing said shaker;

obtaining a test output of said at least second detector; and comparing said test output to said baseline output to determine an amount of total chlorine in said volume of liquid.

8. A system for measuring turbidity, chlorine content and color of a liquid, said system comprising: a sample holder operable for retaining, from a continuous flow of said liquid, a sample volume of said liquid; at least a first detector operable for detecting illumination from said sample volume of liquid at a 90-degree angle with respect to an illumination beam generated by an illuminator and impinging on said sample volume of liquid, thereby measuring a turbidity of said sample volume of liquid; and at least a second detector operable for detecting illumination from said sample volume of liquid at a 180-degree angle with respect to said illumination beam, thereby measuring a color of said sample volume of liquid and thereby measuring a chlorine content of said sample volume of liquid; and a holder cleaning assembly comprising a shaker, said holder cleaning assembly operable for cleaning said sample holder; wherein said cleaning assembly is configured to clean said holder by a method comprising: retaining, from said continuous flow of said liquid, a cleaning volume of said liquid in said holder; repeatedly displacing said shaker between said first position and second position for a first period of time; releasing said cleaning volume of said liquid from said holder;

retaining, from said continuous flow of said liquid, a test volume of said liquid in said holder; actuating said illuminator; and analyzing outputs of said at least first detector and said at least second detector to ascertain whether illumination generated by said illuminator has been detected by both said at least first detector and said at least second detector.

9. A system for measuring turbidity, chlorine content and color of a liquid according to claim 8 and also comprising one or more element functionality ascertaining means, selected from illumination beam functionality operable for ascertaining that said illuminator is operable to properly generate said illumination beam, and detector functionality operable for ascertaining that said at least first detector and said at least second detector are functioning properly.

10. A system for measuring turbidity, chlorine content and color of a liquid according to claim 8, and also comprising
    at least a third detector operable for detecting illumination from said sample volume of liquid at a 45-degree angle with respect to said illumination beam; and
    at least a fourth detector operable for detecting illumination from said sample volume of liquid at a 150-degree angle with respect to said illumination beam.

11. A system for measuring turbidity, chlorine content and color of a liquid according to claim 8, and wherein said measuring said turbidity of said sample volume of liquid, comprises: actuating said illuminator at a first current level.

12. A system for measuring turbidty, chlorine content and color of a liquid according to claim 11, and wherein said lookup table is based on a pre-calibrated light intensity/turbidty curve for said first detector, and wherein turbidity values in said lookup table are based on nephelometric analysis.

13. A system for measuring turbidity, chlorine content and color of a liquid, said system comprising: a sample holder operable for retaining, from a continuous flow of said liquid, a sample volume of said liquid; at least a first detector operable for detecting illumination from said sample volume of liquid at a 90-degree angle with respect to an illumination beam generated by an illuminator and impinging on said sample volume of liquid, thereby measuring a turbidity of said sample volume of liquid; and at least a second detector operable for detecting illumination from said sample volume of liquid at a 180-degree angle with respect to said illumination beam, thereby measuring a color of said sample volume of liquid and thereby measuring a chlorine content of said sample volume of liquid; wherein said measuring said chlorine content of said sample volume of liquid comprises: actuating said illuminator and obtaining a baseline output of said at least second detector; pumping a predetermined amount of a free chlorine indicator and a free chlorine buffer solutions into sample volume of liquid and mixing said sample volume of liquid by employing a shaker; and obtaining a first test output of said at least second detector; and comparing said first test output to said baseline output to determine an amount of free chlorine in said volume of liquid.

14. A system for measuring turbidity, chlorine content and color of a liquid according to claim 13 and wherein said measuring said chlorine content of said sample volume of liquid also comprises:
    pumping a predetermined amount of a total chlorine indicator solution into sample volume of liquid and mixing said sample volume of liquid by employing said shaker;
    obtaining a second test output of said at least second detector; and
    comparing said second test output to said baseline output to determine an amount of total chlorine in said volume of liquid.

15. A system for measuring turbidity, chlorine content and color of a liquid according to claim 13, and wherein said free chlorine indicator is at least one of DPD 1, DPD3 and DPD4.

* * * * *